(12) United States Patent
Cho

(10) Patent No.: US 7,413,640 B2
(45) Date of Patent: Aug. 19, 2008

(54) FOLDABLE, ELECTRIC-CURRENT CONDUCTIVITY BIOSENSOR

(75) Inventor: Ching-Hsin Cho, Taipei (TW)

(73) Assignees: Biomedix Taiwan, Taipei (TW); Biomedix, Inc., Fremont, CA (US)

( * ) Notice: Subject to any disclaimer, the term of this patent is extended or adjusted under 35 U.S.C. 154(b) by 827 days.

(21) Appl. No.: 10/842,520

(22) Filed: May 11, 2004

(65) Prior Publication Data
US 2005/0252769 A1    Nov. 17, 2005

(51) Int. Cl.
*G01N 27/26*    (2006.01)
(52) U.S. Cl. .............................. 204/403.01; 204/403.02
(58) Field of Classification Search ................. 204/416, 204/418, 400–405
See application file for complete search history.

(56) References Cited

U.S. PATENT DOCUMENTS 6,299,757 B1 * 10/2001 Feldman et al. ............. 205/775
2003/0196894 A1 * 10/2003 Cai et al. ................ 204/403.01

FOREIGN PATENT DOCUMENTS

TW    541942    4/1993

OTHER PUBLICATIONS

English Translation of Patent TW 541942; Chou, Chin-hsing; Published Apr. 30, 1993.*

* cited by examiner

*Primary Examiner*—Patrick Ryan
*Assistant Examiner*—J. Christopher Ball
(74) *Attorney, Agent, or Firm*—Rosenberg, Klein & Lee

(57) ABSTRACT

An electric-current biosensor has a support, an electrode film, a conductive film, a bioactivity layer, and an adhesive layer. The support has a first support and a second support with a concave having a testing port therein. The electrode film has a first electrode film disposed on the first support and a second electrode film disposed on the second support. The first electrode film has a positive electrode film and a negative electrode film, which are formed with an interval slit therebetween. The conductive film has a positive and negative conductive films electrically connecting with the positive and negative electrode films, respectively. The bioactivity layer is disposed on the first electrode film and forms an activity area. The activity area covers at least some portions of the positive and negative electrode films. The adhesive layer is disposed between the first and second supports for bonding together.

8 Claims, 3 Drawing Sheets

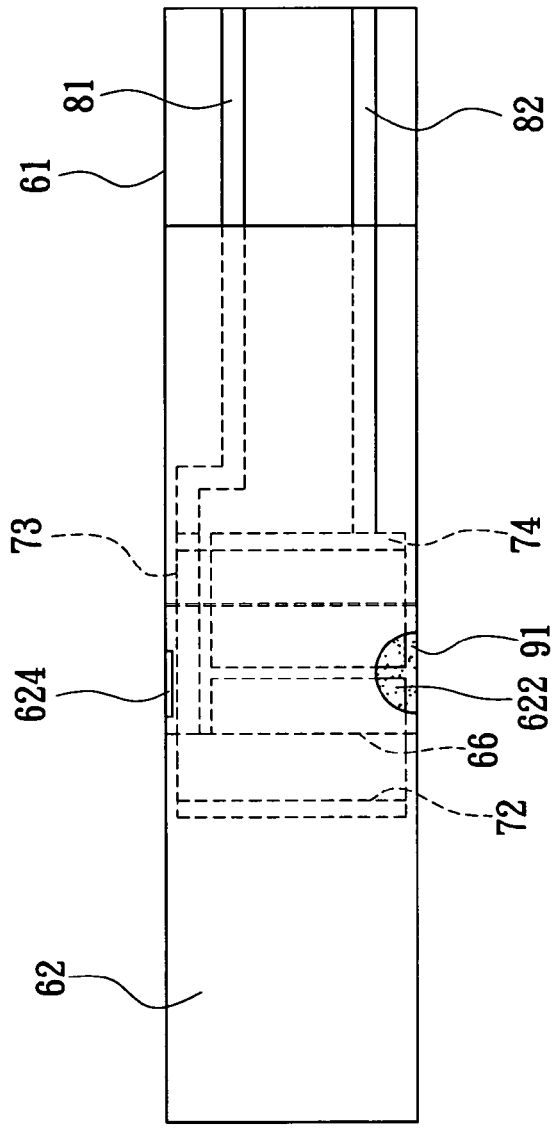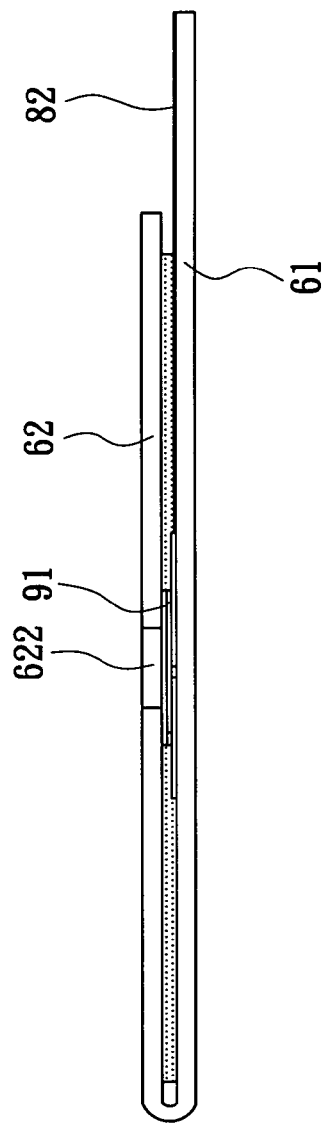

FOLDABLE, ELECTRIC-CURRENT CONDUCTIVITY BIOSENSOR

BACKGROUND OF THE INVENTION

1. Field of the Invention

The present invention relates to an electric-current biosensor, and particularly to an electric-current biosensor that can increase electric-current on a conductive film for testing blood glucose concentration more accurately.

2. Description of the Prior Art

The present simple way of blood glucose determination usually uses an electric-current biosensor and applies a blood sample on the biosensor. The biosensor will accrue oxidation-reduction reaction with the sample and produce electric ions. The ions accrue an electric current on the electric-current biosensor. Then, the electric-current biosensor is inserted into a meter for comparing and analyzing the current, thereby determining the blood glucose concentration.

The applicant has received R.O.C. Patent No. 541942 for an electric-current biosensor. It improved the disadvantage of small reaction area and provided a larger electrode contacting area for lifting the determination accuracy. Referring to the FIGS. 1 and 2, unfolded top and folded top views of biosensors according to the prior art are shown. The biosensor has a support 10, electrode film 20, conductive film 30, bioactivity layer 40, and an adhesive layer 50. The biosensor 10 has a first support 11' a second support 12, and a folding line 13' is formed between the first support 11' and the second support 12 for covering the second support 12 on the first support 11'. The second support 12 is shorter than the first support 11' and is formed with a testing opening 121. The electrode film 20 has a first electrode film 21 and a second electrode film 22. The first electrode film 21 is disposed on the first support 11' and has a positive electrode film 23 and a negative electrode film 24. The second electrode film 22 is disposed on the second support 12 and around the testing opening 121. The conductive film 30 is disposed on the first support 11', and has a positive conductive film 31 and a negative conductive film 32 separate from the positive conductive film 31. The positive and negative conductive films are electrically connected to the positive electrode film 23 and the negative electrode film 24, respectively. The bioactivity layer 40 is disposed on the first electrode film 21, and formed with an activity area 41. The activity area 41 covers at least some portions of the first positive electrode film 23 and the negative electrode film 24. The second support 12 is formed with a mating activity area 16 corresponding to the activity area 41, and the mating activity area 16 is against and close to the activity area 41 when the second support 12 covers the first support 11'. The adhesive layer 50 is disposed on the second support 12 and does not cover the mating activity area 16 and an operating area 51 formed on an end of the second support 12.

When applying the blood sample into the testing opening 121, the sample and the activity area 41 of the bioactivity layer 40 will causes a reaction and release electric ions. The ions will act between the electrode film 20 and the conductive film 30, then the biosensor further cooperates with a meter for comparing the current and analyzing the glucose concentration to get the blood glucose concentration.

Although the prior art raises the accuracy of blood glucose determination, it still has areas, which could be improved. For example, it is not so easy to apply the blood sample into the testing opening 121. Application of the blood sample to the biosensor rather than into the testing opening 121 is a source of inconvenience to the user. Moreover, after the blood sample is applied into the testing opening 121, it mainly spreads vertically toward the positive electrode film 23 and the negative electrode film 24. The ions spread less in the horizontal direction. However, the positive electrode film 23 and the negative electrode film 24 are arranged parallel along a horizontal direction, and the spreading direction of the ions results in a weak current in the horizontal direction.

Therefore, the electric-current biosensor of the prior art still has some inconveniences and disadvantages to be improved. The inventor, after investigation and research, thus provides the present invention of logical design for improving the above-mentioned imperfections.

SUMMARY OF THE INVENTION

An object of the present invention is to provide an electric-current biosensor ensuring that a blood sample reacts effectively on a activity area and the ions spreading effectively toward positive and negative electrode films for increasing electric current and improving the accuracy of blood glucose determination.

In order to achieve the above objects, the present invention provides an electric-current biosensor, which comprises a support, an electrode film, a conductive film, a bioactivity layer, and an adhesive layer. The support has a first support and a second support. The second support is concave with a testing port in a middle portion of a side thereof. The electrode film has a first electrode film disposed on the first support and a second electrode film disposed on a middle portion of the second support. The first electrode film has a positive electrode film and a negative electrode film, and the positive electrode film and the negative electrode film are formed with an interval slit therebetween. The interval slit extends vertically and inwardly from a side edge of the first support. The conductive film has positive and negative conductive films, which connect with the positive electrode film and the negative electrode film, respectively. The bioactivity layer is disposed on the first electrode film and forms an activity area. The activity area covers at least some portions of the positive electrode film and the negative electrode film. The adhesive layer is disposed between the first and second supports to bond the first and second supports together, and the testing port is disposed on the activity area.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 5 is a top view of a folded electrical-current biosensor according to the present invention; and FIG. 6 is a side view of a folded electrical-current biosensor according to the present invention.

DESCRIPTION OF THE PREFERRED EMBODIMENT

Figure 1:
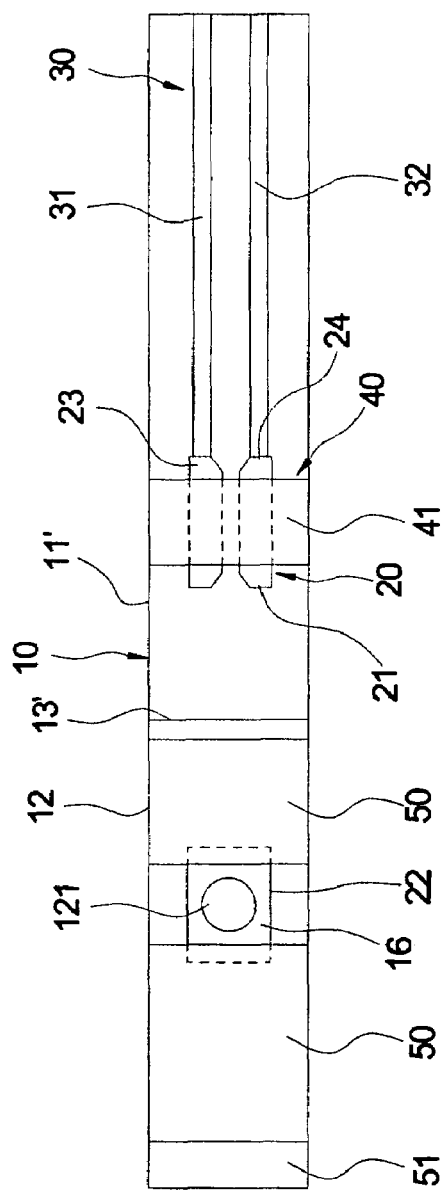
FIG. 1 is a top view of a unfolded electrical-current biosensor of prior art.
Figure 2:
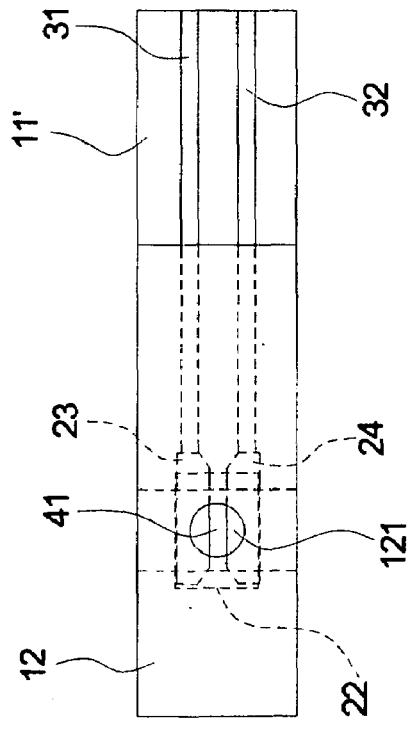
FIG. 2 is a side view of a unfolded electrical-current biosensor of prior art.
Figure 3:
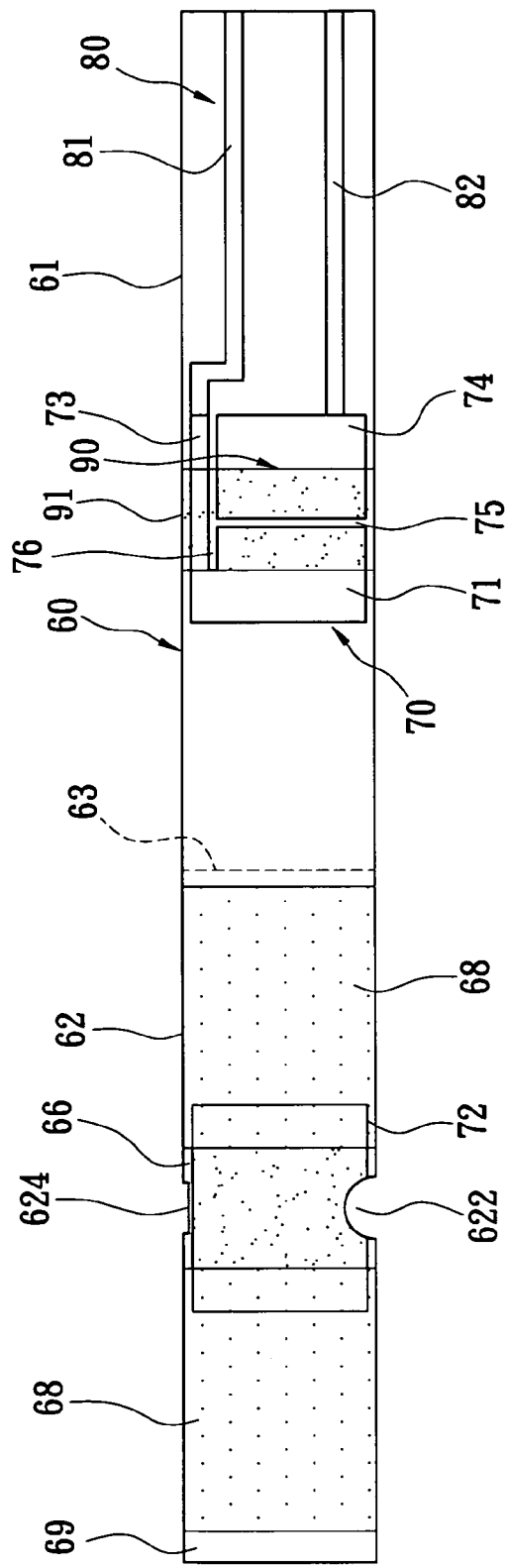
FIG. 3 is a top view of a unfolded electrical-current biosensor according to the present invention.
Figure 4:
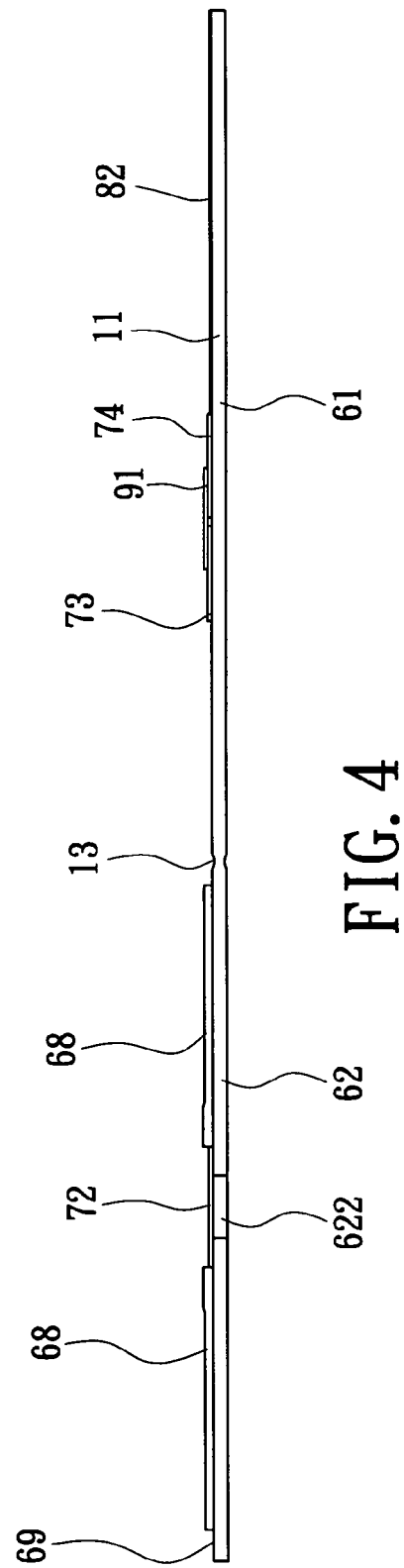
FIG. 4 is a side view of a unfolded electrical-current biosensor according to the present invention.

Referring to the FIGS. 3 and 4, the top and side views of a unfolded electrical-current biosensor according to the present invention are illustrated. An electric-current biosensor according to the present invention comprises a support 60, an electrode film 70, a conductive film 80, a bioactivity layer 90, and an adhesive layer 68.

The support 60 has a first support 61 and a second support 62. A folding line 63 is formed between the first support 61 and the second support 62 for folding and covering the second support 60 on the first support 61. The second support 62 is shorter than the first support 61. The second support 62 is concave with a testing port 622 in a middle portion of a side thereof. The testing port 622 is shaped as a semicircle or another shape.

The electrode film 70 has a first electrode film 71 disposed on the first support 61, and a second electrode film 72 is disposed on a middle portion of the second support 62. The first electrode film 71 has a positive electrode film 73 and a negative electrode film 74. The positive electrode film 73 and the negative electrode film 74 are formed with an interval slit 75 therebetween. The interval slit 75 extends vertically and inwardly from a side edge of the first support 61. A top end 76 of the interval slit 75 extends laterally to the conductive film 70, or extends to two sides and forms a T-shaped interval slit 75.

The conductive film 80 has a positive conductive film 81 and a negative conductive film 82 electrically connected to the positive electrode film 73 and the negative electrode film 74, respectively. The bioactivity layer 90 is disposed on the first electrode film 71 and forms an activity area 91. The activity area 91 covers at least some portions of the positive electrode film 73 and the negative electrode film 74. The composition of the bioactivity layer 90 is disclosed in the above-mentioned patent of the applicant, and consists of:

(1) Enzyme, such as glucose oxidase . . . etc.;

(2) Enzyme protective agent, such as albumin, dextrin, dextran, or amino acid . . . etc.;

(3) Conductive medium, such as potassium . . . etc.;

(4) Surfactant, such as TritonX-100, TritonX-405, TritonX-114, sodium lauryl sulfate, polyoxyethylenesorbitan monolaurate (Tween20), Tween40, Tween60, Tween80, another water surfactant, or detergent;

(5) Buffer solution, i.e. slats, such as phosphate buffer solution . . . etc.; and (6) Water, such as distilled water.

These are mixed in a proper ratio and applied to form the activity area 91 by titration. A mating activity area 66 is formed on the second support 62 corresponding to the activity area 91, so that the mating activity area 66 is against and close to the activity area 91 when the second support 62 covers the first support 61.

The adhesive layer 68 is disposed between the first and second supports 61, 62 to bond the first and second supports 61, 62 together, and the testing port is disposed on the activity area 91. In this embodiment, the adhesive layer 68 is disposed on the second support 62 and on two sides of the second electrode film 72, and does not cover an operating area 69 at one side of the second support 62.

The present invention is further characterized by the second support 62 further comprising a ventilating cutout 624 opposite the testing port 622, so that the blood sample spreads more smoothly.

Referring to FIGS. 5 and 6, the second support 62 of the electric-current biosensor covers the first support 61 according to the folding line 63, and the first and second supports 61, 62 are bonded together via the adhesive layer 68. The testing port 622 mates with the activity area 91 of the first support 61, an uncovered portion of the positive electrode film 73, the negative electrode film 74, and the interval slit 75.

After applying a blood sample on the electric-current biosensor of the present invention, by, for example piercing one finger, bringing it into contact with the testing port 622 and moving it toward the support 60, the sample will spread inwardly along a seam between the second support 62, the bioactivity layer 91, and the interval slit 75. The sample will react with the bioactivity layer 91 of the activity area 90 and release ions. The ions effectively move between the electrode film 70 and the conductive film 80. Then the biosensor further cooperates with a meter for comparing the current and analyzing the glucose concentration to get the blood glucose concentration.

A summary of the characteristics and advantages of the electric-current biosensor, is as follows:

The testing port of the present invention is formed on one side edge of the support, so that the blood sample will spread more effectively to react with the bioactivity layer 91 of the activity area 90.

After applying the sample to the testing port 622, the sample spreads inwardly along the interval slit 75, and the ions produced through reaction of the sample and the bioactivity layer 91 will distribute more widely over the positive electrode film 73 and the negative electrode film 74, so that the testing current is more stable.

Although the present invention has been described with reference to the preferred embodiments thereof, it will be understood that the invention is not limited to the details thereof. Various substitutions and modifications have suggested in the foregoing description, and other will occur to those of ordinary skill in the art. Therefore, all such substitutions and modifications are intended to be embraced within the scope of the invention as defined in the appended claims.

What is claimed is:

1. An electric-current biosensor, comprising:
   a support, having a first and second supports, the second support having a testing port formed on a side thereof;
   a positive electrode film and a negative electrode film disposed on the first support and a second electrode film disposed on a middle portion of the second support, wherein the positive electrode film and the negative electrode film are formed with an interval slit therebetween, and the interval slit extends vertically and inwardly from a side edge of the first support;
   a conductive film, having positive and negative conductive films electrically connected to the positive electrode film and negative electrode film, respectively;
   a bioactivity layer, disposed on the positive electrode film and the negative electrode film and forming an activity area, the activity area covering at least some portions of the positive electrode film and the negative electrode film; and
   an adhesive layer, disposed between the first and second supports to bond the first and second supports together, the testing port is disposed on the activity area; wherein the second support is folded on the first support to expose a portion of the positive electrode film, a portion of the negative electrode film, and a front end of the interval slit having the testing port.

2. The electric-current biosensor as in claim 1, wherein a folding line is formed between the first support and the second support.

3. The electric-current biosensor as in claim 1, wherein the second support is shorter than the first support.

4. The electric-current biosensor as in claim 1, wherein the testing port is semicircular in shape.

5. The electric-current biosensor as in claim 1, wherein the second support further comprises a ventilating cutout opposite the testing port.

6. The electric-current biosensor as in claim 1, wherein the interval slit extends laterally from a top end thereof to the conductive film.

7. The electric-current biosensor as in claim 1, wherein a top end of the interval slit extends to two sides and is T-shaped.

8. The electric-current biosensor as in claim 1, wherein the adhesive layer is disposed on the second support and disposed on two sides of the second electrode film.

* * * * *